United States Patent [19]

Sabatelli et al.

[11] Patent Number: 5,230,874
[45] Date of Patent: Jul. 27, 1993

[54] SUNSCREEN AGENTS, SUNSCREEN COMPOSITIONS AND METHODS FOR PREVENTING SUNBURN

[75] Inventors: Anthony D. Sabatelli, Hamilton, Ohio; Josephine A. Spirnak, New Haven, Conn.

[73] Assignee: The Procter & Gamble Company, Cincinnati, Ohio

[21] Appl. No.: 925,943

[22] Filed: Aug. 5, 1992

Related U.S. Application Data

[60] Division of Ser. No. 638,129, Jan. 7, 1991, Pat. No. 5,160,731, which is a division of Ser. No. 54,046, Jun. 2, 1987, Pat. No. 4,999,186, which is a continuation-in-part of Ser. No. 879,725, Jun. 27, 1986, abandoned.

[51] Int. Cl.$^5$ .............. A61K 7/42; A61K 7/44; C07C 49/76; C07C 49/82
[52] U.S. Cl. .................... 424/59; 424/47; 424/60; 424/63; 514/938; 514/944; 568/331; 568/334; 568/335; 568/336
[58] Field of Search ............. 568/331, 334, 335, 336; 424/59, 60

[56] References Cited

U.S. PATENT DOCUMENTS

| | | | |
|---|---|---|---|
| 2,392,361 | 1/1946 | Britton & Monroe | 260/474 |
| 3,148,934 | 9/1964 | Brookens & Havens | 8/4 |
| 3,636,077 | 1/1972 | Stauffer | 260/471 R |
| 3,676,471 | 7/1972 | Eggensperger, et al. | 260/410.5 |
| 3,751,563 | 8/1973 | Richardson | 424/60 |
| 3,936,419 | 2/1976 | Wang & Irick | 260/45.8 N |
| 3,937,810 | 2/1976 | Mathur, et al. | 424/62 |
| 3,980,617 | 9/1976 | Jacquet, et al. | 260/47 UA |
| 4,002,733 | 1/1977 | Degen & Lucas | 424/59 |
| 4,115,547 | 9/1978 | Degen & Lucas | 424/60 |
| 4,264,581 | 4/1981 | Kerkhof & Herrold | 424/60 |
| 4,279,930 | 7/1981 | Hall, et al. | 568/334 |
| 4,387,089 | 6/1983 | De Polo | 424/59 |
| 4,421,739 | 12/1983 | Bouillon, et al. | 424/47 |
| 4,584,190 | 4/1986 | Tejima, et al. | 424/59 |
| 4,867,964 | 9/1989 | Forestier, et al. | 424/59 |
| 4,937,370 | 6/1990 | Sabatelli | 560/045 |
| 4,999,186 | 3/1991 | Sabatelli & Spirnak | 424/60 |
| 5,041,282 | 8/1991 | Sabatelli & Spirnak | 424/59 |
| 5,138,089 | 8/1992 | Sabatelli | 560/50 |

FOREIGN PATENT DOCUMENTS

| | | | |
|---|---|---|---|
| 0154928 | 9/1985 | EPO | A61K/7.44 |
| 2456731 | 12/1980 | France | C07C/129.12 |
| 57/80356 | 5/1982 | Japan | C07C/117.08 |
| 61/078715 | 9/1984 | Japan | 424/059 |
| 350461 | 1/1961 | Switzerland | 39b/22.01 |
| 1291917 | 10/1972 | United Kingdom | A61K/7.00 |
| 1473483 | 5/1977 | United Kingdom | A61K/7.42 |
| 1553094 | 9/1979 | United Kingdom | A61K/7.42 |
| 1557580 | 12/1979 | United Kingdom | A61K/7.42 |
| 2028131A | 3/1980 | United Kingdom | A61K/7.42 |
| 2098868A | 12/1982 | United Kingdom | A61K/7.42 |
| 2149789A | 6/1985 | United Kingdom | A61K/7.42 |
| 2706782 | 9/1977 | West Germany | A61K/7.44 |

OTHER PUBLICATIONS

Akin, Rose, Chamness & Marlow, "Sunscreen Protection Against Drug-Induced Phototoxicity in Animal Models", Toxicology and Applied Pharmacology, vol. 49 (1979), pp. 219-224.

(List continued on next page.)

Primary Examiner—Dale R. Ore
Attorney, Agent, or Firm—Milton B. Graff, IV; Steven J. Goldstein; Jack D. Schaeffer

[57] ABSTRACT

The present invention relates to novel sunscreen agents which have the ability to absorb both UVA and UVB wavelength radiation. The sunscreen agents comprise a specific type of UVA-absorbing chromophore covalently bonded to a specific type of UVB-absorbing chromophore. The chromophore moieties are covalently bonded together such that the electron systems of these moieties are not directly coupled.

The present invention further relates to sunscreen compositions containing the hereinbefore described type of sunscreen agents. Furthermore, the present invention relates to methods for protecting the skin of humans or lower animals from the effects of UVA and UVB wavelength radiation. This method comprises topically applying to the skin an effective coating of a sunscreen composition of the present invention.

11 Claims, No Drawings

OTHER PUBLICATIONS

Balogh, Durmis, Holcik & Karvas, "Volatility of Ingredients in Relation to Processing Possibilities of Polymer Mixtures", Plasty. Kauc., vol. 14, No. 7 (1977), pp. 204–207 (Chemical Abstract Service Abstract No. 87:185422b, *Abstract Only*).

Cumpelik, "Sunscreens at Skin Application Levels: Direct Spectrophotometric Evaluation", Journal of the Society of Cosmetic Chemistry, vol. 31 (1980), pp. 361–366.

Destrade, Nguyen & Gasparoux, "Mesogenic and Nonmesogenic Central Rigid Cores", Mol. Cryst. Liq. Cryst., vol. 59, No. 3-4 (1980), pp. 273–288 (Chemical Abst. Service Abstract No. 93:58557y, *Abstract Only*) (1980).

Grammaticakis, "Contribution à l'Etude de l'Absorption dans l'U.-V. Moyen et le Visible de Queleques Aldèhydes et Cètones Aromatiques ainsi que Certains de Leurs Dèrivives Fonctionnels", Bulletin de La Societe Chimique de France, Article No. 164 (1953), pp. 821–826.

Grammaticakis, "Contribution à l'Etude de l'Absorption dans l'U.-V. Moyen et le Visible des Composes Carbonyles Aromatiques et de Leurs Derives", Bulletin de La Societe Chimique de France, Article No. 174 (1953), pp. 865–872.

Jacquet, Mahieu & Panantoniou, "UV-Absorbing Polymers for Protecting the Human Body", Rev. Gen. Coautch. Plast., vol. 54, No. 575 (1977), pp. 85–88 (Chemical Abstract Service Abstract No. 89:6867x, *Abstract Only*) (1975).

Sayre, Agin, LeVee & Marlow, "A Comparison of In Vivo and In Vitro Testing of Sunscreen Formulas", Photochemistry and Photobiology, vol. 29, No. 3 (March, 1979), pp. 559–566.

Temchin, Burmistrov, Skripko, Burmistrova, Kokhanov, Gushchina & Rosantsev, "Efficiency of Light Stabilizers for Polymers Studied by Accelerated Methods", Vysokomol. Soedin., Ser. A, vol. 15(5), (1973), pp. 1038–1048 (Chemical Abst. Service Abstract No. 79:79679r, *Abstract Only*).

Temchin & Burmistrov, "Dependence of the Efficiency of Photostabilizers for Polypropylene upon Their Chemical Structure", Mater. Plast. Elastomeri, (1975), pp. 41–44 (Chemical Abstract Service Abstract No. 83:60222x, *Abstract Only*).

Tirrell, "Polymeric Ultraviolet Absorbers", Polymer News, vol. 7, No. 3 (1981), pp. 104–110.

Tsukerman, S.V., V.P. Maslennikova, V.M. Nikitchenko & V.F. Lavrushin, "Electronic Spectra of Isomeric para-Dichalcones and para-Dichalcone Analogs", Zhurnal Prikladnoi Spektroskopii, vol. 12, No. 1 (January, 1970), pp. 91–96 (published translation).

Tsukerman, S.V., V.P. Maslennikova, V.M. Nukutchenko, B.F. Lavrushin, "Halochromism of Isomeric Paradichalcones and Some of Their Analoques", Ukr. Khimicheskii Zhurnal, No. 6 (1972), pp. 597–602 (with translation).

Volkotrub, Rubtsova, Lukovnikov, Skripko & Burmistrova, "Light Stabilizer for Bulk-Polymerized Polystyrene", Plast. Massy., (1974), p. 76 (Chemical Abstract Service Abstract No. 82:86978c, *Abstract Only*).

SUNSCREEN AGENTS, SUNSCREEN COMPOSITIONS AND METHODS FOR PREVENTING SUNBURN

This is a division of application Ser. No. 07/638,129, filed on Jan. 7, 1991 now U.S. Pat. No. 5,160,731; which is a division of application Ser. No. 07/054,046, filed on Jun. 2, 1987, now U.S. Pat. No. 4,999,186 issued Mar. 12, 1991; which is a continuation-in-part of application Ser. No. 06/879,725 filed on Jun. 27, 1986, now abandoned.

BACKGROUND OF THE INVENTION

The present invention relates to novel compounds useful as sunscreen agents, which compounds have ability to absorb sunlight in both the UVA and UVB wavelength range. The present invention further relates to novel skin protection compositions which are effective at protecting skin from both UVA and UVB wavelength sunlight. Finally, the present invention also relates to methods for protecting the skin from the effects of UVA and UVB wavelength irradiation, such as sunburn and sun-induced aging of the skin.

The damaging effects of sunlight on skin are well documented. In spite of this, people are forced to be in the sun for long periods of time due to their occupations. Others are in the sun for long periods through their leisure time activities and/or a desire to have a tanned appearance.

The major short term hazard of prolonged exposure to sunlight is erythema (i.e., sunburn). The 290 to 320 nanometer wavelength ultraviolet radiation range, which is designated by the cosmetic industry as being the "UVB" wavelength range, is the most effective type of UV radiation for producing erythema. The 320 to 400 nanometer wavelength ultraviolet radiation range, which is designated by the cosmetic industry as being the "UVA" wavelength range, also produces erythema.

In addition to the short term hazard of erythema caused by UVA and UVB sunlight, there are also long term hazards associated with this UV radiation exposure. One of these long term hazards is malignant changes in the skin surface. Numerous epidemiologic studies have been conducted, and the results demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity. The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499-511 (American Pharmaceutical Association, Washington, D.C.; 1982); Grove and Forbes, "A Method for Evaluating the Photoprotective Action of Sunscreen Agents Against UV-A Radiation", *International Journal of Cosmetic Science*, 4, pp. 15-24 (1982); and U.S. Pat. No. 4,387,089, to DePolo, Issued Jun. 7, 1983; the disclosures of all of which are incorporated herein by reference. Hence, although the immediate effects of ultraviolet radiation may be cosmetically and socially gratifying, the long-term effects are cumulative and potentially serious.

Sunscreen compositions comprising mixtures of molecules which absorb at different UV wavelengths and which thereby protect the skin are known in the art. For example, U.S. Pat. No. 4,264,581, to Kerkhof et al (issued Apr. 28, 1981), discloses a sunscreen composition containing a mixture of 2-ethylhexyl dimethyl-para-amino benzoate and 2-hydroxy-4-methoxy-benzophenone; U.S. Pat. No. 3,751,563, to Richardson (issued Aug. 7, 1973), discloses a sunscreen composition containing a mixture of 2-ethoxyethyl para-methoxycinnamate, amyl para-dimethylamino benzoate, homomenthyl salicylate, and 2-hydroxy-4-methoxybenzophenone; and U.S. Pat. No. 3,636,077, to Stauffer (issued Jan. 18, 1972), discloses sunscreen compositions containing salts of 5-benzoyl-4-hydroxy-2-methoxy benzene sulfonic acid and 4-aminobenzoic acids or esters.

Notwithstanding the foregoing developments, there remains a continuing need to identify new compounds and compositions which are effective for protecting the skin from ultraviolet radiation in both the UVA and UVB radiation ranges. It is accordingly an object of the present invention to provide compounds which are effective sunscreening agents for both UVA and UVB radiation, as well as sunscreen compositions containing these sunscreen compounds. It is a further object of the present invention to provide methods for protecting the skin of humans or lower animals from the effects of exposure to UVA and UVB wavelength radiation by employing sunscreening compounds and compositions of the present invention.

It is a further object of the present invention to provide sunscreening agents and compositions which are not readily absorbed by the skin; which have increased sunscreen protection and decreased chance for allergy, irritation, or toxicity problems resulting from use; and which are resistant to rub off. A still further object is to provide sunscreen agents and compositions which provide a constant and even protection against both UVA and UVB radiation; which are cosmetically acceptable; and which are readily formulated into sunscreen compositions.

These and other objects will become readily apparent from the detailed description which follows.

SUMMARY OF THE INVENTION

The present invention relates to sunscreen agents which are effective for absorbing ultraviolet radiation in both the UVA and UVB wavelength range. These sunscreen agents are compounds which have both a selected UVA-absorbing chromophore moiety and a selected UVB-absorbing chromophore moiety covalently linked together in the same molecule. These chromophore moieties are linked such that the electron systems of the chromophore moieties are not directly coupled via this covalent linkage.

The present invention further relates to sunscreen compositions. These compositions comprise a pharmaceutically-acceptable sunscreen carrier and a compound generally characterized by having both a UVA-absorbing chromophore moiety and a UVB-absorbing chromophore moiety. Again, the chromophore moieties are covalently linked such that the electron systems of these moieties are not directly coupled via the covalent linkage.

Finally, the present invention also relates to methods for protecting the skin of humans or lower animals from the effects of UVA and UVB wavelength radiation, such as sunburn and sun-induced aging of the skin. Such methods comprise topically applying to the skin of the human or lower animal an effective coating of a sunscreen agent useful in the present invention.

DETAILED DESCRIPTION OF THE INVENTION

Sunscreen agents

The sunscreen agents useful in the present invention are those whose molecules have two distinct chromophore moieties which exhibit different ultraviolet radiation absorption spectrums. In particular, one of the chromophore moieties absorbs predominantly in the UVB radiation range, and the other absorbs strongly in the UVA radiation range. Further, these molecules have the chromophore moieties linked in the molecule by covalent bonding, with this covalent linkage not permitting the electron systems of the chromophore moieties to be coupled through the linkage.

More particularly, one of the chromophore moieties is characterized as being effective for strongly absorbing radiation in the UVA range when that chromophore moiety is isolated in an independent molecule. The other chromophore moiety is characterized as being effective for absorbing radiation predominantly within the UVB range when that chromophore moiety is isolated in an independent molecule. Finally, the linking moiety which covalently incorporates these two types of chromophore moieties into a single molecule is one which does not allow the electron systems of the two chromophore moieties to be coupled directly with each other. Thus, the sunscreen agents useful in the present invention are compounds having the general structure:

In this general structure, the X group is a UVA-absorbing chromophore that is a substituted, carbonyl-containing, aromatic ring-containing moiety. This UVA-absorbing moiety when isolated as an independent chromophore would exhibit at least one absorption maximum (designated herein as λmax, and described more fully hereinafter) within the wavelength range of from about 320 to about 400 nm. This absorption maximum would exhibit a molar absorptivity value (designated herein as "ε", and calculated as described hereinafter) of at least about 9,000, preferably at least about 20,000, and most preferably at least about 30,000.

The Z group in the above general structure is a UVB-absorbing chromophore that is a substituted, carbonyl-containing, aromatic ring-containing moiety. This UVB-absorbing moiety, when isolated as an independent chromophore, would exhibit a molar absorptivity value, ε, of at least about 4,000, preferably at least about 15,000, and most preferably at least about 25,000, for at least one wavelength within the range of from about 290 to about 320 nm. Preferably, when present as the sole chromophore in a molecule as hereinafter defined, the Z group exhibits at least one absorption maximum λmax within the range of from about 290 to about 320 nm. This absorption maximum preferably has a molar absorptivity value ε of at least about 4,000, more preferably at least about 15,000, and most preferably at least about 25,000. Finally, when present as the sole chromophore in a molecule as hereinafter defined, the Z group furthermore should not exhibit a λmax having an ε greater than about 9,000 for any wavelength above about 320 nm.

The third component of the above general structure, i.e., the Y group, is any linking moiety which covalently bonds the X and Z chromophore moieties into one molecule, but which separates the electron systems of the two chromophore moieties such that the two chromophore moieties do not have their electron systems directly coupled with each other. For example, the Y linking moiety may be a straight or branched chain alkyl group having from about 1 to about 6 carbon atoms, a straight or branched chain alkyloxy group having from about 1 to about 6 carbon atoms, or straight or branched alkylamino group having from about 1 to about 6 carbon atoms.

The sunscreen agents of the present invention preferably absorb light in the visible wavelength range (i.e., above about 400 nm) only weakly or not at all. The compounds are therefore either only lightly colored (e.g., light yellow or cream colored) or are essentially white. This is desirable for cosmetic reasons. Thus, the sunscreen agents preferably do not have an ε of greater than about 500 for any wavelength above about 400 nm, and most preferably the ε is essentially zero for any wavelength above about 400 nm.

It is further preferred that the compounds of the present invention be lower molecular weight compounds, preferably having a molecular weight of less than about 2,500, and most preferably less than about 1,000. Furthermore, the compounds are preferably liquids above about 10° C.

Specifically, examples of suitable X chromophore moieties useful in the sunscreen compounds of the present invention include:

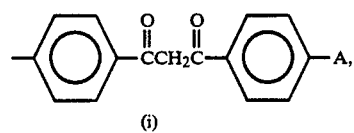

(i)

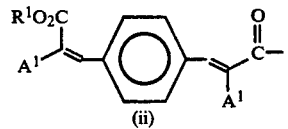

(ii)

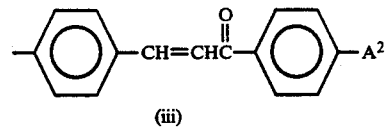

(iii)

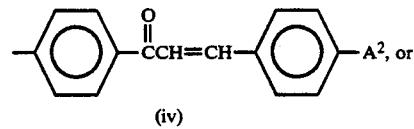

(iv)

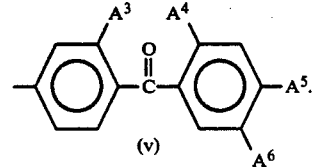

(v)

In all the preceding formulae, each A is a substituent independently selected from the group consisting of R, —OR, —NR$_2$, or —SO$_3$H, or its pharmaceutically-acceptable salt or ester; each $A^1$ is independently —CN or —$CO_2R^1$; each $A^2$ is independently —OR or —$NR_2$; each $A^3$ is independently H or OH; each $A^4$ and $A^5$ are, independently, R or OR, and wherein further either $A^3$ or $A^4$ must be OH; each $A^6$ is independently H or —$SO_3H$, or its pharmaceutically-acceptable salt or ester; each R is independently H, straight or branched chain alkyl having from about 1 to about 20 carbon atoms, $(CH_2CH_2O)_p$—H, or $(CH_2CH(CH_3)O)_p$—H, wherein p is an integer from 1 to about 8, and preferably p=1 to about 3; and each $R^1$ is independently straight or branched chain alkyl having from about 1 to about 20 carbon atoms.

Preferred as the X chromophore moiety are the groups

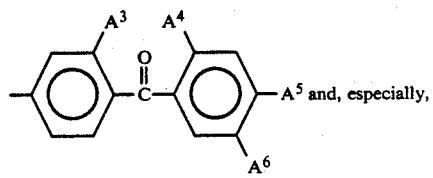

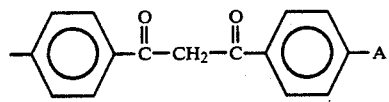

Preferably, either $A^3$ or $A^4$ is OH, with the other group being H; $A^5$ is R; and $A^6$ is H. Most preferably, $A^3$ is OH, and $A^4$, $A^5$ and $A^6$ are H. A is preferably R, and most preferably A is H.

Also, specific examples of the Z chromophore moieties useful in the sunscreen compounds of the present invention include:

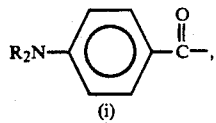
(i)

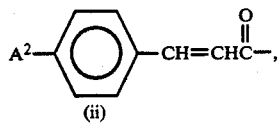
(ii)

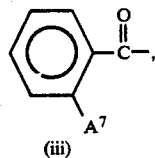
(iii)

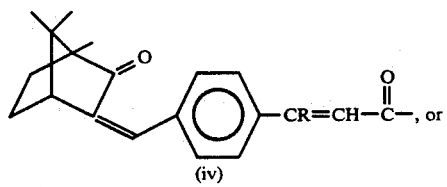
(iv)

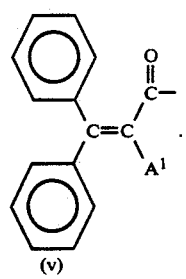
(v)

In these preceding formulae, each $A^7$ is independently —OR or —$O_2C$—$R^1$, except that both $A^7$ and $A^3$ (described hereinbefore for the X groups) are not —OH; and the $A^1$, $A^2$, R and $R^1$ substituent groups are as described hereinbefore for the substituted X groups.

Preferred as the Z chromophore moiety are the groups

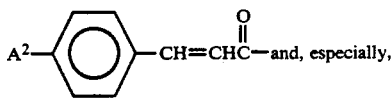

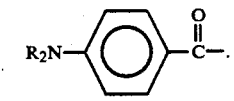

Preferably, —$NR_2$ is —$NR^1_2$. Both $R^1$ groups may be different alkyl groups. Particularly preferred is one $R^1$ group having more than about 2 carbon atoms (especially branched-chain alkyl groups, e.g., 2-ethyl-hexyl), the other $R^1$ group being methyl or ethyl, especially methyl. Alternatively preferred, both $R^1$ groups are the same alkyl group, preferably 2-ethyl-hexyl. Also preferred is $A^2$ being —OR or —$NR_2$ (preferably the —$NR_2$ is —$NR^1$ as described hereinbefore). Most preferred $A^2$ is —$OCH_3$, —$OCH_2CH_3$, OH, or —$NR^1_2$ (wherein one $R^1$ group has more than about 2 carbon atoms, especially branched-chain alkyl, and the other $R^1$ group is methyl or ethyl, especially methyl).

The Y linking moieties useful in the compounds of the present invention include the generically described moiety:

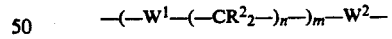

wherein each $W^1$ and $W^2$ is, independently, selected from the group consisting of a single bond, or, preferably, a moiety selected from the group of O or NR (wherein R is as described hereinbefore); n is an integer of 1 or greater, preferably n equals an integer from 1 to about 6; m is an integer of 1 or greater, preferably m is 1 or 2; and each $R^2$ group is independently selected from the group consisting of H, OH, or straight or branched chain alkyl having from 1 to about 20 carbon atoms, preferably $R^2$ is H, OH, methyl or ethyl.

Preferred Y linking moiety groups include:

—O—(—$CH_2$—)$_n$—O—, wherein n is an integer from 1 to about 6;

—NH—(—$CH_2$—)$_n$—NH—, wherein n is an integer from 1 to about 6;

—(—O—$CH_2CH_2$—)$_n$—O—, wherein n is 1 or 2;

—(—NH—$CH_2CH_2$—)$_n$—NH—, wherein n is 1 or 2;

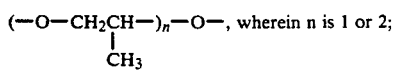, wherein n is 1 or 2;

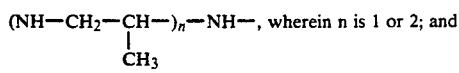, wherein n is 1 or 2; and

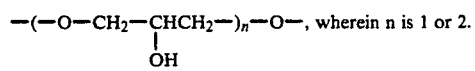, wherein n is 1 or 2.

The most preferred Y group is —OCH₂CH₂O—.

Preferred sunscreen agents of the present invention have the general structures:

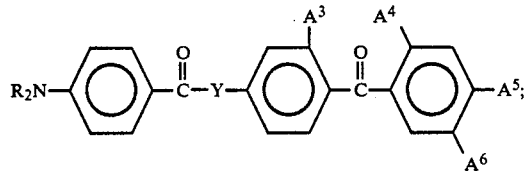

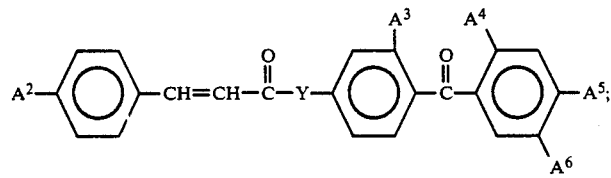

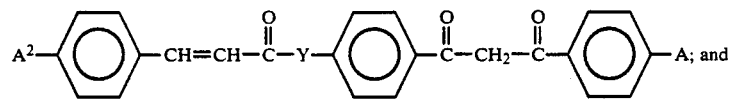

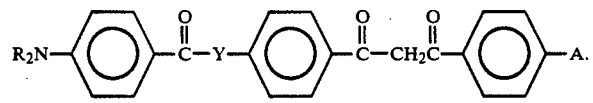

Especially preferred are the last two structures, with the last structure being most preferred. The Y moiety and substituents are preferably as described hereinbefore. The most preferred Y moiety is —O—(—CH₂—)$_n$—O—; wherein n is an integer from 1 to about 6, and especially n=2.

Specific sunscreen agents of the present invention include, for example:

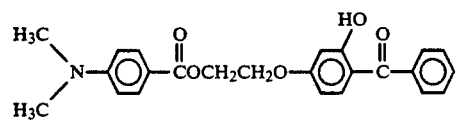

4-N,N-dimethylaminobenzoic acid 4-ester of 2-hydroxy-4-(2-hydroxyethoxy)benzophenone ("Compound 1");

4-methoxycinnamic acid 4-ester of 2-hydroxy-4-(2-hydroxyethoxy)benzophenone ("Compound 2");

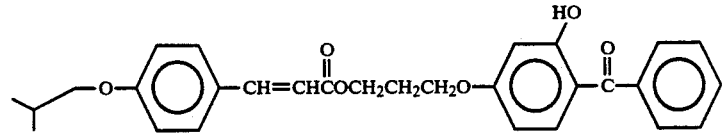

4-(2-methylpropoxy)cinnamic acid 4-ester of 2-hydroxy-4-(2-hydroxyethoxy)benzophenone ("Compound 3");

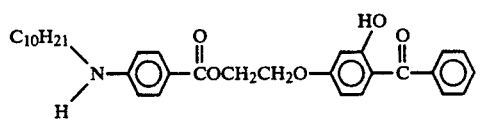

4-N-decylaminobenzoic acid 4-ester of 2-hydroxy-4-(2-hydroxyethoxy)benzophenone ("Compound 4");

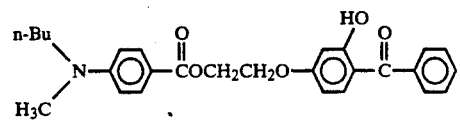

4-N,N-butylmethylaminobenzoic acid 4-ester of 2-hydroxy-4-(2-hydroxyethoxy)benzophenone ("Compound 5");

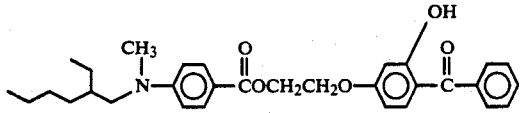

4-N,N-(2-ethylhexyl)methylaminobenzoic acid 4-ester of 2-hydroxy-4-(2-hydroxyethoxy)benzophenone ("Compound 6");

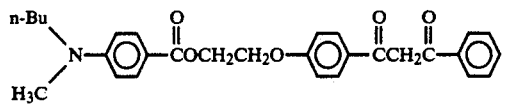

4-N,N-butylmethylaminobenzoic acid ester of 4-(2-hydroxyethoxy)dibenzoylmethane ("Compound 7");

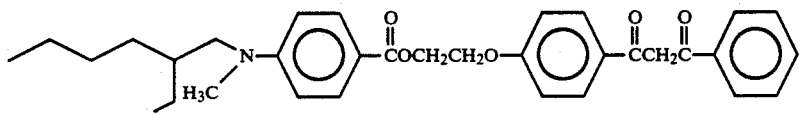

4-N,N-(2-ethylhexyl)methylaminobenzoic acid ester of 4-(2-hydroxyethoxy)dibenzoylmethane ("Compound 8");

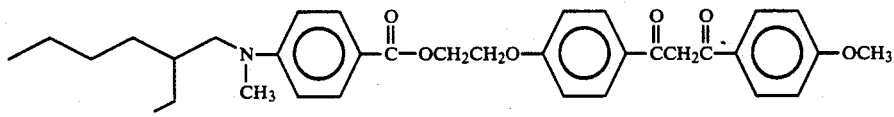

4-N,N-(2-ethylhexyl)methylaminobenzoic acid ester of 4-(2-bromoethoxy)-4'-methoxydibenzoylmethane ("Compound 9");

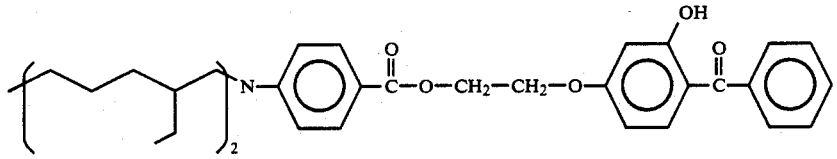

N,N-di-(2-ethylhexyl)-4-aminobenzoic acid ester of 2-hydroxy-4-(2-hydroxyethoxy)benzophenone ("Compound 10"); and

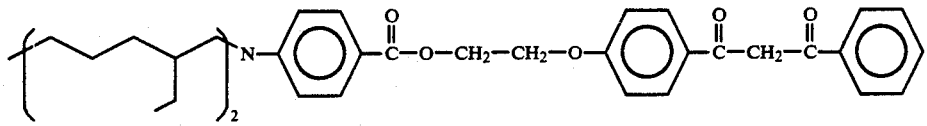

N,N-di-(2-ethylhexyl)-4-aminobenzoic acid ester of 4-(2-hydroxyethoxy)dibenzoylmethane ("Compound 11").

The sunscreen agents of the present invention can be prepared from commercially-available, chromophore-containing molecules. Typically, the synthesis of the sunscreen agents will be achieved by an esterification or amidation reaction. Synthesis techniques which are generally applicable for synthesizing sunscreen agents of the present invention are taught, for example, in U.S. Pat. No. 4,002,733, issued Jan. 11, 1977, to Degen et al.; and in U.S. Pat. No. 4,115,547, issued Sep. 19, 1978, to Degen et al.; the disclosures of both these patents being incorporated herein by reference. Representative procedures for synthesizing the sunscreen agents of the present invention are provided in the Examples hereinafter.

The term "pharmaceutically-acceptable salts and esters", as used herein, means those ester or salt forms of the sunscreen agents which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (e.g., mono-, di-, tri- and tetra-substituted amine which are substituted with methyl and/or ethyl) salts. Preferred are the sodium, potassium, and ammonium salts. Pharmaceutically acceptable esters include straight or branched chain alkyl ester having from 1 to about 20 carbon atoms, preferably the methyl or ethyl ester.

The term "independent chromophore", as used herein, means the chromophore moiety (i.e., either the X or Z group) when it is bonded to —O—$R^3$ (wherein $R^3$ represents a short chain alkyl group, e.g., methyl or ethyl; preferably methyl) rather than the chromophore moiety being bonded to the Y linking moiety within the X—Y—Z compound. For example, independent chromophores of Compound 5 described hereinbefore are the ethyl ester of 4-N,N-butylmethylaminobenzoic acid and 2-hydroxy-4-methoxy-benzophenone. Also as an example, independent chromophores of Compound 8 described hereinbefore are the methyl ester of 4-N,N-(2-ethylhexyl)methylaminobenzoic acid and 4-methoxydibenzoylmethane.

The term "molar absorptivity value", as used herein, is a quantitative measure of the ability of a molecule to absorb ultraviolet light at a specified wavelength. The molar absorptivity value is expressed at a particular wavelength of light as the molar absorption coefficient (represented herein by "ε" which is expressed in units of liter/mole cm), which is calculated by the equation:

$$\epsilon = \frac{A}{lc}$$

wherein "l" is the path length (in centimeters) of the absorbing media through which the light passes; "c" is the concentration of the chromophore molecule (in moles per liter); and "A" is the "absorbance". The absorbance is calculated from the observed difference in the intensity of the particular wavelength of light before and after passing through the chromophore-molecule-containing absorbing media. Thus, the absorbance is calculated by the equation:

$$A = \log_{10}\frac{I_0}{I}$$

wherein "$I_0$" is the intensity of a particular wavelength of incident radiation on an absorbing path; and "I" is the intensity of the same particular wavelength of transmitted radiation which has passed through the absorbing path.

The calculation of the molar absorptivity value for a particular wavelength of light is well-known in the art, and is taught in more detail in *Atlas of Spectral Data and Physical Constants for Organic Compounds*, 2nd Ed., Vol. I, pp. 399-408 (Grasselli and Ritchey, Editors; CRC Press, Inc., Cleveland, Ohio, 1975), the disclosures of which are incorporated herein by reference. Instruments useful for making the intensity measurements for the calculation of the molar absorptivity value are also well-known in the art (e.g., Varion DMS-100 and Beckman DU-7). Molar absorptivity values for representative compounds of the present invention are provided in the Examples hereinafter.

The term "absorption maximum", as used herein, means a wavelength of radiation at which the chromophore-containing molecule has the greatest molar absorptivity value relative to wavelengths immediately above and below the absorption maximum wavelength. Thus, in the typical spectrum of UV-radiation absorption, an absorption maximum is easily identified as a peak in the graph of the spectrum generated by the instrument measuring the UV absorption. Absorption maximum (designated herein as λmax) are provided for representative sunscreen compounds of the present invention in the Examples hereinafter.

The sunscreen agents useful in the present invention have several desirable properties relative to a simple mixture of a UVA-absorbing molecule with a UVB-absorbing molecule. One benefit is the certainty of providing both UVA and UVB protection at the same site on the skin. A mixture of molecules may lack this uniformity due to non-uniform distribution onto the skin surface and/or selective penetration by one type of molecule through the skin versus the other type of molecule. A related benefit is that the sunscreen agents of the present invention provide a constant relative proportion of UVA to UVB protection because one chromophore cannot be more readily lost from the skin (e.g., by a higher rate of rub-off or skin penetration) than the other chromophore. Another benefit is that the sunscreen agents of the present invention are absorbed more slowly by the skin than mixtures of the independent chromophores. This translates into longer duration of protection for the skin, and less potential for skin irritation resulting from absorption by the skin. Furthermore, the sunscreen agents useful in the present invention provide this long-lasting, constant UV radiation protection at least as effectively as a freshly-applied mixture of independent chromophores, and in some instances the protection is stronger and more broad-spectrum than the mixture. (The ability of the compounds of the present invention, and of mixtures of independent chromophores, to absorb UV radiation may be measured by in vitro methods known generally in the art, such as those taught in Sayre et al., "A Comparison of in vivo and in vitro Testing of Sunscreening Formulas", *Photochem. Photobiol.*, 29, 559-566 (1979), the disclosures of which are incorporated herein by reference.) Some of the compounds of the present invention may also be more resistant to wash-off by water from sweat or swimming.

The sunscreen agents of the present invention typically comprise from about 0.1% to about 99.9% by weight of the sunscreen compositions of the present invention, preferably from about 1% to about 20%, and most preferably from about 5% to about 15%.

Pharmaceutically-acceptable Sunscreen Carriers

In addition to a sunscreen agent as described hereinbefore, the sunscreen compositions of the present invention essentially contain a pharmaceutically-acceptable sunscreen carrier. The term "pharmaceutically-acceptable sunscreen carrier", as used herein, means one or more substantially non-irritating compatible filler diluents which are suitable for topical application to the skin of a human or lower animal. The term "compatible", as used herein, means that the components of the carrier must be capable of being comingled with the sunscreen agent, and with each other, in a manner such that there is no interaction which would substantially reduce the efficacy of the composition during use for protecting the skin from the effects of UVA and UVB wavelength radiation. Pharmaceutically-acceptable sunscreen carriers must, of course, be of sufficiently high purity and sufficiently low toxicity to render them suitable for topical administration to the human or lower animal.

The sunscreen compositions of the present invention contain pharmaceutically-acceptable sunscreen carriers selected as appropriate for the formulation desired. For example, it is possible to prepare sunscreen compositions of the present invention in the form of organic solvent solutions, aqueous emulsions, gels, or aerosol formulation. Preferred are sunscreen compositions of the present invention formulated as aqueous emulsions. The pharmaceutically-acceptable sunscreen carriers useful in the compositions of the present invention include, for example, water, oils, fats, waxes, synthetic polymers, emulsifiers, surfactants, perfumes, dyes, preservatives, artificial tanning agents (e.g., dihydroxyacetone), and conventional sunscreening agents (e.g., octyl N,N-dimethyl-paraaminobenzoate; 2-hydroxy-4-methoxybenzophenone).

Water is typically the major component of the sunscreen compositions of the present invention. Generally, water is present at a level of from about 50% to about 99% by weight of the composition, preferably from about 70% to about 96%, and most preferably from about 75% to about 85%.

Emulsifiers are preferably included in the sunscreen compositions of the present invention, preferably comprising from about 1.5% to about 10% by weight of the composition, and most preferably from about 2% to about 5%. Preferred emulsifiers are anionic or nonionic although other types may also be used. Suitable emulsifiers are disclosed in, for example, U.S. Pat. No. 3,755,560, issued Aug. 28, 1973, to Dickert et al.; U.S. Pat. No. 4,421,769, issued Dec. 20, 1983, to Dixon et al.; and McCutcheon's *Detergents and Emulsifiers*, North American Edition, 1983; with the disclosures of these references being incorporated herein by reference.

Types of emulsifiers useful in the sunscreen compositions of the present invention include ethoxylated fatty acids, ethoxylated esters, ethoxylated ethers, ethoxylated alcohols, phosphated esters, polyoxyethylene fatty ether phosphates, fatty acid amides, acyl lactylates, soaps and mixtures thereof. Fatty alcohols such as cetyl and stearyl alcohol, and cetearyl alcohol are also regarded as emulsifiers for purposes of the present invention.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium steroyl-2-lactylate and calcium stearoyl-2-lactylate. Soaps are also acceptable emulsifiers. The soaps may be formulated in situ in processing the compositions and are preferably alkali metal or triethanolamine salts of long-chain fatty acids. Such soaps include sodium stearate, triethanolamine stearate and the similar salts of lanolin fatty acids.

Also preferred for use in the compositions of the present invention is a copolymer of ethylene and acrylic acid. These monomers:

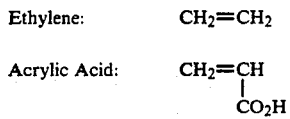

are present in polymeric form as follows:

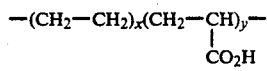

wherein the ratio of x:y is from about 1:24 to about 1:9. The weight average molecular weight is from about 3,500 to about 4,500, preferably from about 4,000 to about 4,300.

The compositions of the present invention may also contain in addition to the aforementioned components, a wide variety of additional oil soluble materials and/or water soluble materials.

Among the oil soluble materials are non-volatile silicone fluids such as polydimethyl siloxanes with viscosities ranging from about 10 to about 100,000 centistokes at 25° C. These siloxanes are available from Dow Corning Corporation as the Dow Corning 200 series.

Other oil soluble materials include fatty acid alcohols such as cetyl alcohol and stearyl alcohol; esters such as cetearyl palmitate, lauryl myristate and isopropyl palmitate; oils such as castor oil, jojoba oil, cottonseed oil, peanut oil and sesame oil; waxes such as petrolatum, ceresin wax, carnauba wax, beeswax, and castor wax; lanolin, its derivatives and components such as acetylated lanolin, lanolin alcohols and lanolin fatty acids. Sterols such as cholesterol and phytosterol are also useful herein.

These optional oil phase materials may individually comprise up to about 20% by weight of the total sunscreen composition, preferably up to about 10%.

Additional water soluble materials may also be present in the compositions of this invention. Included are humectants such as glycerine, sorbitol, propylene glycol, alkoxylated glucose and hexanetriol; tyrosine; thickening agents such as carboxyvinyl polymers (Carbopols ®—offered by B. F. Goodrich Company, such polymers are described in detail in U.S. Pat. No. 2,798,053, issued Jul. 2, 1957 to Brown, incorporated herein by reference); ethyl cellulose, polyvinyl alcohol, carboxymethyl cellulose, vegetable gums and clays such as the Veegum ® (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corp.), EDTA, methylisothiazolinone and imidazolidinyl ureas (Germall 115—Sutton Laboratories); and an alkaline agent such as sodium hydroxide or potassium hydroxide to neutralize, if desired, part of the fatty acids or thickeners which may be present.

The water phase materials may individually comprise up to about 20% by weight of the total sunscreen composition, preferably up to about 10%.

The present compositions may also contain agents suitable for aesthetic purposes such as perfumes and/or dyes.

The pH of the sunscreen compositions herein is preferably in the range of from about 4.5 to about 9.

For an aqueous emulsion sunscreen composition of the present invention, the mean particle size of the dispersed oil phase materials (e.g., sunscreen agent, polymer, perfumes, etc.) dispersed in the aqueous phase may be in the range of from about 5 to about 10 microns with greater than about 75% of the particles being less than about 12 microns.

The pharmaceutically-acceptable sunscreen carriers, in total, typically comprise from about 0.1% to about 99.9% by weight of the sunscreen compositions of the present invention, preferably from about 80% to about 99%, and most preferably from about 85% to about 95%.

The compositions of the present invention may be prepared using the method described in the examples hereinafter.

Method for Preventing Sunburn

The present invention further relates to a method for protecting the skin of humans or lower animals from the effects of UVA and UVB wavelength radiation, such as sunburn and premature aging of the skin. Such a method comprises topically applying to the human or lower animal an effective coating of a sunscreen agent of the present invention, or, preferably, of a sunscreen composition of the present invention. The term "effective coating", as used herein, means a film of sunscreen agent sufficient to substantially reduce the amount of UVA and UVB wavelength light which reaches the skin's surface. Typically, an effective coating of the skin is from about 0.5 mg sunscreen agent of the present invention/cm$^2$ skin to about 5 mg sunscreen agent of the present invention/cm$^2$ skin.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

Synthesis of Compound 1

(a) Synthesis of 4-(2-bromoethoxy)-2-hydroxybenzophenone

A 2000 mL, 1 neck round-bottomed flask containing a magnetic stir bar is charged with 2,4-dihydroxybenzophenone (85.6 g, 0.40 mol, Aldrich Chemical Co., Milwaukee, Wis.). To this is added a solution of sodium hydroxide (16.0 g) dissolved in 320 mL of water. Next, 1,2-dibromoethane (105.6 g, 0.56 mol) dissolved in 320 ml of ethanol is added. The reaction mixture is heated to reflux with stirring for 16 hours. The reaction vessel is then transferred to a rotary evaporator where the liquids are removed at aspirator pressure at 80° C. A brown solid is obtained which is suspended in 180 mL of acetone and stirred for 1 hour at 45° C. This mixture is filtered and the filtrate poured into 2 L of water containing 20 g of sodium carbonate yielding 65 grams of a tan precipitate. This material is recrystallized from approximately 100 mL of ethanol to give 55.3 g (0.17 mol, 43%) of a light tan solid m.p. 87°-89.5° C.

$^1$H NMR (60 MHz, CDCl$_3$): 3.7 (t,2H, J=5 Hz); 4.4 (t, 2H, J=5 Hz); 6.5 (m, 2H); 7.2 (m, 6H); 11.3 (s, 1H).

(b) Synthesis of Sunscreen Compound 1

A 100 mL, round-bottomed flask equipped with a magnetic stir bar is charged with 4-N,N-dimethylaminobenzoic acid (0.520 g, 3.14 mmol, Aldrich Chemical Co., Milwaukee, Wis.). To this is added 1 equivalent (0.075 g) of sodium hydroxide dissolved in 25 mL of water and 25 mL of methanol, and the mixture heated to dissolve the acid. The solvents are removed by rotary evaporation giving the salt of the acid. To this is added 25 mL of DMF and tetrabutylammonium bromide (0.051 g, 0.157 mmol). Next, 2-hydroxy-4-(2-bromoethoxy)benzophenone (1.00 g, 3.14 mmol, from Example 1a hereinbefore) dissolved in 15 mL DMF is added. The mixture is heated to 110° C. for 16 hours during which time a golden yellow solution is formed. The solvent is removed by rotary evaporation (0.5 Torr, 60° C.) to yield a solid. This is stirred in acetone and the insoluble sodium bromide is filtered off. The filtrate is rotovaped to yield 1.9 g of a brown oil. Purification by flash chromatography (silica gel, 60/40 hexane/acetone) yields a light yellow solid m.p. 121°-122° C. Anal. calcd. for C$_{24}$H$_{23}$O$_5$N: C, 71.10; H, 5.72; O, 19.73; N, 3.45. Found: C, 70.84; H, 5.68; O, 20.36; N, 3.15. The UV spectrum of Compound 1 (isopropanol solution) exhibits a λmax=312 nm ($\epsilon$=34,670).

EXAMPLE 2

Synthesis of Compound 3

(a) Synthesis of 4-(2-methylpropoxy)benzaldehyde

A 1000 mL, 1 neck, round-bottomed flask equipped with a magnetic stirrer and reflux condenser is charged with 4-hydroxybenzaldehyde (33.18 g, 0.272 mol), 100 ml of ethanol, and a solution of potassium hydroxide (20.42 g, 0.309 mol) in 100 mL of ethanol. The reaction mixture is heated with stirring for one-half hour. Next 1-iodo-2-methylpropane (100 g, 0.543 mol) is added and the mixture refluxed for 12 hours. After cooling, the solvents are removed by rotary evaporation to yield a brown solid which is added to a separatory funnel containing 500 mL ether and 500 mL of 5% aqueous sodium carbonate. The layers are separated and the aqueous phase is washed with ether (2×500 mL). The combined ether layers are washed with pH 12 sodium hydroxide solution (5×200 mL) until the washes are colorless. The organic solution is then washed with brine (100 mL) and dried over magnesium sulfate. After filtration and removal of the solvents by rotary evaporation, a viscous yellow liquid is obtained. This material is purified by Kugel-Rohr distillation to give 22.3 g (0.125 mol, 46%) of a colorless liquid.

$^1$H NMR (60 MHz, CDCl$_3$): 1.00 (d, 6H); 2.0 (m, 1H); 3.65 (d, 2H); 6.75, 6.90, 7.60, 7.75 (aa'bb' quartet, 4H); 9.75 (s, 1H).

(b) Synthesis of 4-(2-methylpropoxy)cinnamic acid

A 500 mL, 1 neck, round-bottomed flask equipped with a magnetic stirrer and reflux condenser is charged with 4-(2-methylpropoxy)benzaldehyde (17.84 g, 0.100 mol, as from Example 2a), malonic acid (10.42 g, 0.100 mol), and 19 mL of pyridine. The mixture is heated with stirring in a 130° C. oil bath for 24 hours, then stirred at room temperature for 16 hours. The reaction mixture is then poured into a separatory funnel containing 300 mL of pH 12 aqueous sodium hydroxide and 300 mL of ether. The layers are separated and the aqueous phase washed with 150 mL of ether. The aqueous phase is then acidified with concentrated hydrochloric acid to bring the pH to 1 whereupon the powdery white acid precipitates out. The mixture is chilled in an ice/salt bath and the solid collected giving 5.89 g (0.027 mol, 27%) of product, m.p. 161°-164° C.

$^1$H NMR (60 MHz, CDCl$_3$); 1.05 (d, 6H); 2.0 (m, 1H); 3.75 (d, 2H); 6.3 (d, 1H, J=16 Hz); 6.8, 6.95, 7.3, 7.45 (aa'bb' quartet, 4H); 7.7 (d, 1H, J=16 Hz); 10.9 (br s, 1H).

(c) Synthesis of Sunscreen Compound 3

Sunscreen Compound 3 is prepared by essentially the same method as the synthesis of Sunscreen Compound 1 described in Example 1b hereinbefore, except that 4-(2-methylpropoxy)cinnamic acid (from Example 2b hereinbefore) is used in place of the 4-N,N-dimethylaminobenzoic acid. The crude material is purified by flash chromatography (silica gel, 60/40 hexane/acetone) to yield a light yellow solid, m.p. 113.5°-115° C. Anal. calcd. for C$_{28}$H$_{28}$O$_6$: C, 73.03; H. 6.13; O, 20.84. Found: C, 72.93; H. 6.07; O, 20.66. The UV spectrum of Compound 3 (isopropanol solution) exhibits a λmax=312 ($\epsilon$=35,480).

EXAMPLE 3

Synthesis of Compound 5

(a) Synthesis of 4-N,N-butylmethylaminobenzoic acid

A 500 mL, 3 necked, round-bottomed flask equipped with an overhead stirrer, dropping funnel, and reflux condenser is charged with 4-N-methylaminobenzoic acid (25.0 g, 0.165 mol, Aldrich Chemical Co., Milwaukee, Wis.) 130 mL of benzene, glacial acetic acid (40.0 g, 38.13 mL), and zinc dust (42.5 g, 0.65 g atom). This mixture is heated to reflux with stirring at which time a dropwise addition of butyraldehyde (29.74 g, 0.412 mol) is begun. After the addition is completed, the reaction mixture is refluxed for an additional 3 hours. The hot solution is filtered through a Celite® filter cake on a medium sintered glass funnel and washed with an additional 100 mL of hot benzene. The filtrate is poured into a separatory funnel containing 200 mL of water and 500 mL of chloroform. The contents are brought to pH approximately 1 with concentrated hydrochloric acid. The chloroform is removed and the aqueous layer is extracted with chloroform (3×150 mL). The combined chloroform extracts are washed with 150 mL of brine and dried over magnesium sulfate. After filtration and removal of the solvents by rotary evaporation and in vacuo drying at 45° C., 28.8 g (0.139 mol, 84%) of a beige solid m.p. 131°–134° C. is obtained.

$^1$H NMR (270 MHz, CDCl$_3$): 0.88 (t, 3H, J=7.4 Hz); 1.29 (m, 2H); 1.51 (m, 2H); 2.94 (S, 3H); 3.30 (t, 3H); 6.54, 6.57, 7.86, 7.89 (aa'bb' quartet, 4H); 14.0 (br s, 1H).

$^{13}$C NMR (67.8 MHz, CDCl$_3$): 13.9, 20.2, 29.0, 38.4, 52.1, 110.4, 115.4, 132.1, 152.8, 172.7.

(b) Synthesis of Sunscreen Compound 5

A 100 mL, round-bottomed flask equipped with a magnetic stirring bar is charged with 80% NaH oil dispersion (0.127 g, 4.23 mmol). Next, 15 mL of HPLC grade DMSO is added and the mixture is heated at 70° C. for 15 min. Then, a solution of 4-N,N-butylmethylaminobenzoic acid (0.77 g, 3.72 mmol, as in Example 3a) dissolved in 5 mL DMSO is added, giving a clear, light amber solution. Next, 4-(2-bromoethoxy)-benzophenone (1.19 g, 3.72 mmol, as in Example 1a) dissolved in 5 mL DMSO is added and the reaction mixture stirred for 3 hours. The mixture is cooled, poured into a separatory funnel containing 50 mL water and 50 mL ether, shaken intimately, and the layers separated. The aqueous layer is extracted with ether (2×50 mL). The combined organic layers are washed with brine and dried over magnesium sulfate. After filtration and removal of the solvents by rotary evaporation, 1.50 g of a yellow oil is obtained. An analytical sample is obtained by flash chromatography (silica gel, 80/20 hexane/acetone) to yield a light yellow viscous oil. Anal. calcd. for C$_{27}$H$_{29}$O$_5$N: C, 72.46; H, 6.53; O, 17.88; N, 3.13. Found: C, 72.05; H, 6.55; O, 17.47; N, 3.29. The UV spectrum of Compound 5 (isopropanol solution) exhibits a λmax=314 (ε=34,670).

EXAMPLE 4

Synthesis of Compound 6

2,4-dihydroxybenzophenone (42.8 g, 0.2 mole) is placed in a 500 ml flask equipped with a stirrer and positive nitrogen. Then 144 ml of deionized water, 160 ml ethanol, 16.0 g (0.2 mole) of 50% sodium hydroxide and 1,2-dibromoethane (63.0 g, 0.33 mole) are added to the flask. This mixture is then heated to reflux for 24 hours. The volatiles are then removed by rotoevaporation to give a solid. This material is heated with 150 ml of ethanol, filtered hot and then allowed to crystalize. After drying for one hour at 50° C. under 0.1 mm of vacuum (m.p. 94°–96° C.) filtration results in 29.5 g of tan needles. This is the desired 4-(2-bromoethyl)-2,4-dihydroxybenzophenone.

N-2-ethylhexyl-N-methyl-4-aminobenzoic acid (15 g, 0.057 mole) is dissolved in 50 ml of methanol followed by addition of sodium hydroxide (4.56 g, 0.057 mole of a 50% solution dissolved in 25 ml of methanol). The volatiles are then removed by rotoevaporation and vacuum drying at 50° C. for 4 hours. The result is 16.1 g of solid. 15.0 g (0.0526 mole) of this solid is placed in a 250 ml flask equipped with a condensor, stirrer, and positive nitrogen. 4-(2-bromoethyl)-2,4-dihydroxybenzophenone (16.8 g, 0.0526 mole) is added to the flask with 150 ml of anhydrous dimethylformamide and 0.2 g of dimethyldioctyldecylammonium bromide and this mixture is heated to 100° C. for 20 hours. After cooling to room temperature, the reaction mixture is poured into 30 ml of deionized water and 250 ml diethyl ether. The water layer is extracted with 250 ml diethyl ether and then the ether layers combined and dried over magnesium sulfate. Rotoevaporation followed by vacuum (0.1 mm) drying at 50° C. for 1 hour results in 28.4 g of liquid which is mostly the desired product: (4-ethylene-2,4-dihydroxybenzophenone) N-2-ethylhexyl-N-methyl-4-aminobenzoate.

EXAMPLE 5

Synthesis of Compound 8

(a) Synthesis of 4-N,N-(2-ethylhexyl)methylaminobenzoic acid

A 1000 mL, 3 necked, round-bottomed flask equipped with an overhead stirrer, dropping funnel, and reflux condenser is charged with 4-N-methylaminobenzoic acid (25.0 g, 0.165 mol Aldrich Chemical Co., Milwaukee, Wis.), 130 mL of toluene, glacial acetic acid (40.0 g), and zinc dust (42.5 g, 0.65 g atom). This mixture is heated to reflux with stirring at which time a dropwise addition of 2-ethylhexanal (84.6 g, 0.66 mol) is begun. After the addition is completed, the reaction mixture is refluxed for 16 hours. TLC analysis (silica gel, 50/50 hexane/acetone) shows that not all of the acid is reacted. An additional 7.0 g of zinc dust and 2 mL of glacial acetic acid is added. After 2 hours of additional reflux, TLC analysis shows the starting acid to be consumed. The hot solution is filtered through a Celite® filter cake on a medium sintered glass funnel and washed with 100 mL of hot toluene. The filtrate is poured into a separatory funnel containing 200 mL of water and 500 mL of chloroform. The mixture is brough to pH approximately 1 with concentrated hydrochloric acid. After shaking intimately, the chloroform layer is drained off and the aqueous layer is extracted with chloroform (3×150 mL). The combined chloroform extracts are washed with 150 mL of brine and dried over magnesium sulfate. After filtration and removal of the solvents by rotary evaporation (0.1 Torr, 100° C. water bath), 40.4 g of a light brown waxy solid is obtained. This material is recrystallized from 120 mL of 90% ethanol to yield 30.2 g of a fluffy white solid, m.p. 55.5°–57.5° C. Anal. calcd. for C$_{16}$H$_{25}$O$_2$N: C, 72.96; H, 9.57; O, 12.15; N, 5.32. Found: C, 73.11; H, 9.62; O, 12.28; N, 5.23.

Alternatively, N-(2-ethylhexyl)-N-methyl-4-aminobenzoic acid can be prepared by the following method. Ethyl 4-aminobenzoate is dissolved in 1;1 acetic acid/ethanol with 2-ethyl hexanal. Then 10% Pd on Carbon (2 kg benzoate/75 g catalyst) is added. This mixture is placed under hydrogen at room temperature for one hour. The reaction is then determined to be complete by TLC. An excess of 40% aqueous formaldehyde is added and the reaction again placed under hydrogen at 30°–35° C. for one hour. The reaction is complete by TLC. The reaction mixture is then filtered through Celite and the solvents removed. The resulting material is partitioned between water and methylene chloride. The methylene chloride layer is then washed with saturated sodium bicarbonate. The resulting methylene chloride layer is then dried over magnesium sulfate and the volatiles are removed after filtration to give the desired product as the ethyl ester. This material is placed in 12 volumes of ethanol/water (65:35) per weight of ethyl ester. Two mole equivalents of sodium hydroxide are added and the mixture refluxed for two hours. The reaction is then complete by TLC. most of the ethanol is removed and more water added followed by the hydrochloric acid. The resulting desired carboxylic acid then precipatates. The total process is close to quantitative. Recrystalization of the product is in 2 kg acid per 4.5 liters of ethanol. About a 70% recovery of material is observed.

(b) Synthesis of 4-hydroxydibenzoylmethane

A 1000 mL, 3 necked, round-bottomed flask equipped with an overhead stirrer, dropping funnel, and reflux condenser is charged with sodium hydride 80% oil dispersion (12.0 g, 0.40 mol) which is washed twice with hexanes. Next, 200 mL of freshly distilled glyme is added and the slurry heated to reflux with stirring. A solution of 4-hydroxyacetophenone (13.62 g, 0.10 mol) dissolved in 100 mL of glyme is added dropwise. The reaction mixture is allowed to reflux for 45 minutes after the addition. Next, a solution of methyl benzoate (13.62 g, 0.10 mol) dissolved in 100 mL of glyme is added dropwise. The reaction mixture is allowed to reflux for 16 hours, after which time most of the glyme was distilled off at aspirator pressure. The pot residue is cooled in an ice bath and 300 mL of ether is added followed by the cautious addition of 200 mL of water. The mixture is poured into a separatory funnel, shaken intimately, and the aqueous layer removed. The ether layer is washed with cold water (2×200 mL) followed by 100 mL of cold 1% aqueous NaOH. The combined aqueous layers are carefully poured onto a mixture of 400 g of ice plus 90 mL of concentrated HCl. The yellowish green solid that precipitates is collected by suction filtration and washed with a little cold water. This material is recrystallized from 95% ethanol to yield 13.1 g of a yellow solid, m.p. 153°–156° C. Anal. calcd. for $C_{15}H_{12}O_3$: C, 74.99; H, 5.03; O, 19.98. Found: C, 74.72; H, 5.02; O, 19.80.

(c) Synthesis of 4-(2-bromoethoxy)dibenzoylmethane

A 500 mL, 1 neck round-bottomed flask containing a magnetic stir bar is charged with 4-hydroxydibenzoylmethane (30.10 g, 0.125 mol, as from Example 4b). To this is added a solution of sodium hydroxide (6.0 g) dissolved in 100 mL of water. Next, 1,2-dibromoethane (46.97 g, 0.250 mol) dissolved in 100 mL of ethanol is added. The deep orange-brown solution is refluxed for 4 hours. TLC analysis (silica gel, 80/20 hexane/acetone) shows starting material still remaining. Additional sodium hydroxide (1.0 g dissolved in a minimum amount of water) and 1,2-dibromoethane (5.0 g) is added. The reaction mixture is allowed to reflux for 16 hours. The solvents are removed by rotary evaporation to give a dark brown solid which is suspended in 200 mL of acetone and stirred at 40° C. for 1 hour. The solids are filtered off and the acetone solution is concentrated to about 50 mL by rotary evaporation. This solution is poured into 600 mL of water containing 6.0 g of sodium carbonate yielding 56.6 g of a yellow precipitate, m.p. 94°–98° C. This material is recrystallized from ethanol.

$^1$H NMR (60 MHz, Acetone-$d_6$): 3.7 (t, 2H); 4.3 (t,2H); 6.8–8.1 (complex, 11H)

(d) Synthesis of Sunscreen Compound 8

A 500 mL, round-bottomed flask equipped with an overhead stirrer, dropping funnel, and reflux condenser is charged with 80% NaH oil dispersion (1.28 g, 42.6 mmol) which is washed with hexane. Next, 100 mL of DMF is added and the slurry heated to 70° C. with stirring, at which time a solution of 4-N,N-(2-ethylhexyl)methylaminobenzoic acid (11.22 g, 42.6 mmol, as from Example 4a) dissolved in 30 mL of DMF is added dropwise. The reaction mixture is stirred for 1 hour. Next, a solution of 4-(2-bromoethoxy)dibenzoylmethane (14.79 g, 42.6 mmol, as from Example 4c) dissolved in 50 mL of DMF is added dropwise. The reaction mixture is allowed to stir for 16 hours at 70° C. Then the reaction mixture is cooled and poured into a separatory funnel containing 200 mL of water and 200 mL of ether, and shaken intimately. The layers are separated and the aqueous layer is extracted with ether (2×200 mL). The combined ether layers are washed with 50 mL of brine and dried over magnesium sulfate. After filtration, the solvents are removed by rotary evaporation (0.5 Torr) to yield an amber oil. An analytical sample is prepared by purification by flash chromatography (silica gel, 90/10 hexane/acetone) and trituration of the chromatographed material with additional 90/10 hexane/acetone. M.P. 73°–75° C. Analysis calcd for $C_{33}H_{39}O_5N$: C, 74.84; H, 7.42; O, 15.10; N, 2.64. Found: C, 74.68; H, 7.47; O, 15.37; N, 2.66. The UV spectrum of Compound 8 (isopropanol solution) exhibits a $\lambda max=317$ ($\epsilon=45{,}570$) and $\lambda max=352$ ($\epsilon=33{,}280$).

EXAMPLE 6

Synthesis of Compound 9

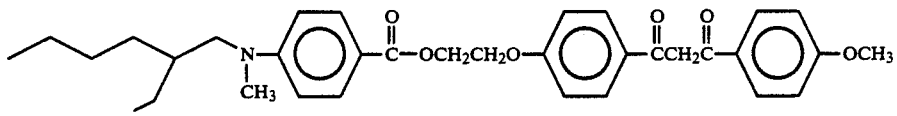

Compound 9

(a) Synthesis of 4-hydroxy-4'-methoxydibenzoylmethane

This compound is prepared by a procedure analogous to the procedure used to prepare 4-hydroxydibenzoylmethane, but using methyl 4-methoxybenzoate in place of the methyl benzoate as used in Example 4b. mp=180°–182° C. Anal. calcd for $C_{16}H_{14}O_4$: C, 71.10; H, 5.22; O, 23.68. Found: C, 71.15; H, 5.54; O, 23.47.

(b) Synthesis of Sunscreen Compound 9

This compound is prepared by essentially the same procedure as used to prepare Sunscreen Compound 8 (as in Example 4d) using 4-N,N-(2-ethylhexyl)methylaminobenzoic acid (as in Example 4a) and 4-(2-bromoethoxy)-4'-methoxydibenzoylmethane (prepared by a procedure analogous to that in Example 4c from the 4-hydroxy-4'-methoxydibenzoylmethane of Example 6a).

EXAMPLE 7

Synthesis of Compound 10

Compound 10 can be synthesized by the same method as Compound 6 except 4-N,N-di-(2-ethylhexyl)aminobenzoic acid is substituted for 4-N-(2-ethylhexyl)-N-methylaminobenzoic acid.

EXAMPLE 7a

Synthesis of Compound 11

Compound 11 can be synthesized by the same method as Compound 8 except 4-N,N-di(2-ethylhexyl)aminobenzoic acid is substituted for 4-N-(2-ethylhexyl)-N-methylaminobenzoic acid.

EXAMPLES 8–14

The following sunscreen compositions are representative of the present invention:

| Component: | Weight % Example # | | | | | | |
|---|---|---|---|---|---|---|---|
| | 8 | 9 | 10 | 11 | 12 | 13 | 14 |
| Sunscreen Compound: | | | | | | | |
| #(1) | 10 | — | — | — | — | 7.5 | — |
| #(3) | — | 3 | — | — | — | — | — |
| #(5) | — | — | 6 | — | — | — | 4.9 |
| #(8) | — | — | — | 10 | — | — | 2.1 |
| #(9) | — | — | — | — | 7.5 | 10 | — |
| Ethylene/Acrylate Copolymer[1] | .75 | 0.25 | 0.45 | 0.75 | 0.75 | 1.25 | 0.5 |
| Glycerin | 3.50 | 6.00 | 5.50 | 4.00 | 3.50 | 2.00 | 5.0 |
| Petrolatum | 1.50 | 2.50 | 2.00 | — | 1.50 | 0.50 | 2.0 |
| Dimethicone[2] | .30 | 0.50 | 0.30 | 0.40 | 0.30 | 0.20 | 0.40 |
| Steareth-100 | .48 | 0.48 | 0.7 | 0.3 | 0.375 | 0.90 | 0.70 |
| Glycerol Monostearate | .32 | 0.32 | 0.8 | 0.7 | 0.875 | 0.80 | 0.30 |
| Cetyl Alcohol | 1.20 | 1.2 | 1.0 | 1.0 | 1.0 | 1.50 | 1.20 |
| Stearic Acid | .52 | .52 | .52 | 0.52 | 0.52 | 0.52 | 0.52 |
| Carbopol 934[3] | .08 | .08 | .15 | 0.09 | 0.18 | 0.20 | 0.10 |
| Carbopol 941[3] | .06 | .06 | .08 | 0.09 | 0.05 | 0.05 | 0.10 |
| Methyl Paraben[4] | .20 | .2 | .2 | .2 | 0.20 | .2 | 0.20 |
| Propyl Paraben | .10 | .1 | .1 | .1 | 0.10 | .1 | 0.10 |
| Imidazolidinyl Urea | .10 | .1 | .1 | .1 | .10 | .1 | 0.10 |
| Tetrasodium EDTA | .10 | .1 | .1 | .1 | .10 | .1 | 0.10 |
| Tyrosine | .10 | .1 | .1 | .1 | .10 | .1 | 0.10 |
| Potassium Hydroxide | .31 | 0.35 | 0.37 | 0.31 | 0.395 | 0.32 | 0.37 |
| Titanium Dioxide | .30 | 0.20 | 0.30 | 0.40 | 0.40 | 0.50 | 0.40 |
| Perfume | .18 | 0.08 | 0.15 | 0.13 | 0.10 | 0.25 | 0.15 |
| Water | 79.90 | 83.86 | 81.08 | 80.71 | 79.455 | 72.91 | 80.66 |
| TOTAL | 100.00 | 100.00 | 100.00 | 100.00 | 100.00 | 100.00 | 100.00 |

[1]Offered by Allied Chemical Company as AC 540A having a weight average molecular weight of 4271 and having 5% ethylene
[2]Polydimethylsiloxane offered by Dow Corning as DC-200
[3]Carboxyvinyl polymers offered by B. F. Goodrich
[4]Preservatives offered by Sutton Laboratories The above compositions can be made by adding the following components as described:

| Part | Material |
|---|---|
| I | Water |
| | Carbopol 934 |
| | Carbopol 941 |
| | Methyl Paraben |
| | Propyl Paraben |
| | Glycerin |
| II | Sunscreen Agents |
| | Cetyl Alcohol |
| | Glycerol Stearate |
| | Steareth-100 |
| | Stearic Acid |

| Part | Material |
|---|---|
| | Dimethicone |
| | Petrolatum |
| | Ethylene/Acrylate Copolymer |
| III | Tetrasodium EDTA |
| | Potassium Hydroxide |
| | Titanium Dioxide |
| IV | Tyrosine |
| | Imidazolidinyl Urea |
| | Perfume |

The composition is made by mixing the water phase (Part I) materials at 71°–99° C. in a scale-mounted mix tank fitted with baffles and an agitator. The oil phase (Part II) is mixed at 71°–110° C. in a separate mix tank fitted with an agitator. Both Part I and Part II are mixed until homogeneous phases are obtained.

The water phase (Part I) is then pumped into the oil phase (Part II) in an amount equal to 60–110% of the oil phase (Part II). This oil/water premix is held at a temperature of from about 71°–99° C. and agitated until a homogeneous mixture is obtained. The oil/water premix is then pumped into the remaining water phase (Part I) and held at a temperature of from about 71°–99° C. Part III ingredients are then added while maintaining agitation and holding the temperature at 71°–99° C. The composition is then passed through a closed vessel equipped with an ultrasonic probe at the flow rate of 0.5–6.5 kg/min. The ultrasonic frequency may range from 15 to 40 kHz. The composition is further processed through a heat exchanger and/or jacket cooling to a temperature of 71°–99° C. The part IV components are then added while maintaining agitation until a homogeneous mixture is obtained.

The composition is then pumped through a heat exchange to cool to 21°-32° C. While waiting to reach steady-state operation, the composition may be recirculated back to the mix tank. The composition is then packed into glass bottles.

The sunscreen composition of Example 11 is rubbed onto the skin of the person in need of protection from UVA and UVB wavelength radiation. A thin layer of this sunscreen composition is applied to the skin which will be exposed to the radiation. This sunscreen composition is easy to apply to skin, and the sunscreen agent is not readily absorbed by the skin or readily rubbed off. Furthermore, it provides a constant and even protection against both UVA and UVB radiation.

EXAMPLE 15

Skin Penetration by Sunscreen Agents of the Present Invention

Skin penetration is done with human abdominal skin (Shriner's Burns Institute) mounted on a ground-glass diffusion cell. The skin surface area exposed is 0.785 cm². The sunscreen agents are applied as a solution (100 microliters) in a vehicle (either ethanol or dimethyl isosorbide). The receiving reservoir is 4.5 ml of vehicle. The reservoir is stirred and maintained at 37° C. Penetration is determined by reading the UV absorbance of the reservoir. Assays are done in triplicate.

Penetration of Sunscreen Agents of the Present Invention vs. Commonly Used Sunscreen Agents

| Sunscreen | Total Material Penetrated in 24 hrs. (ug/cm²) |
|---|---|
| 2-ethylhexyl 4-N,N-dimethylaminobenzoate (ethanol vehicle) | 70 |
| 2-hydroxy-4-methoxybenzophenone (dimethyl isosorbide vehicle) | 21 |
| Compound 5 (dimethyl isosorbide vehicle) | 5 (at 30 hours) |
| Compound 8 (ethanol vehicle) | 13 |

The low amount of skin penetration by the sunscreen agents useful in the present invention provides a uniform layer of protection for the skin against both UVA and UVB radiation. This protection against the UVA and UVB radiation will not vary with time as might occur by using a mixture containing molecules that are absorbed and/or rubbed off at different rates. Also, the relative UVA to UVB protection will not vary with time for the sunscreen agents of the present invention. Furthermore, the protection by the sunscreen agents of the present invention should last longer because it is less readily lost by absorption through the skin. Finally, there is less potential for toxicity (typically in the form of skin irritation) for the sunscreen agents of the present invention due to this low amount of skin penetration.

What is claimed is:

1. A sunscreen compound having the structure:

X—Y—Z wherein (a) —X is a UVA-absorbing moiety selected from the group consisting of those having the structures:

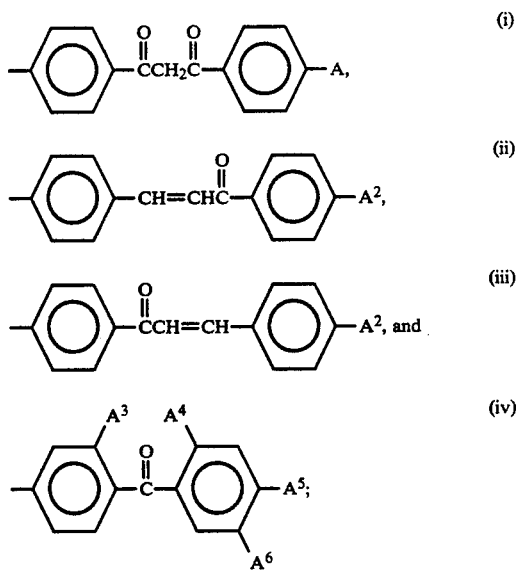

(b) —Z is a UVB-absorbing moiety having the structure:

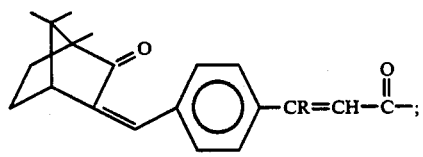

(c) —Y— is a linking moiety having the structure:

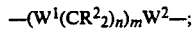

wherein, in the above structures, —W¹— and —W²— are independently selected from the group consisting of a single bond, —O— and —NR—; n is an integer from 1 to about 6; m is 1 or 2; each —R² is independently selected from the group consisting of —H, —OH, straight chain alkyl having from about 1 to about 20 carbon atoms, and branched chain alkyl having from about 1 to about 20 carbon atoms; —A is selected from the group consisting of —R, —OR, —NR₂, and —SO₃H or its pharmaceutically-acceptable salt or ester; —A² is —OR or —NR₂; —A³ is —H or —OH; —A⁴ and —A⁵ are, independently, —R or —OR, and wherein further either —A³ or —A⁴ must be —OH; —A⁶ is —H or —SO₃H or its pharmaceutically-acceptable salt or ester; and each —R is independently selected from the group consisting of —H, straight chain alkyl having from about 1 to about 20 carbon atoms, branched chain alkyl having from about 1 to about 20 carbon atoms, —(CH₂CH₂O)ₚH, and —(CH₂CH(CH₃)O)ₚH, wherein p is an integer from 1 to about 8.

2. The compound of claim 1 wherein —Y— is selected from the group consisting of the following structures:

—O(CH₂)ₙO—, wherein n is an integer from 1 to about 6;

—NH(CH₂)ₙNH—, wherein n is an integer from 1 to about 6;

—(OCH₂CH₂)ₙO—, wherein n is 1 or 2;

—(NHCH₂CH₂)ₙNH—, wherein n is 1 or 2;

—(OCH$_2$CH)$_n$O—, wherein n is 1 or 2;
    |
    CH$_3$

—(NHCH$_2$CH)$_n$NH—, wherein n is 1 or 2; and
    |
    CH$_3$

—(CH$_2$CHCH$_2$)$_n$O—, wherein n is 1 or 2.
    |
    OH

3. The compound of claim 2 wherein —X has the structure:

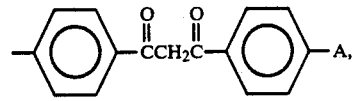      (i)

wherein —A is —R.

4. The compound of claim 3 wherein —Y— is —OCH$_2$CH$_2$O—, —A is —H, and —R is —H.

5. The compound of claim 2 wherein —X has the structure:

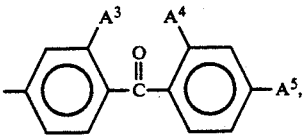

wherein —A$^5$ is —R, and either —A$^3$ or —A$^4$ is —H.

6. The compound of claim 5 wherein —Y— is —OCH$_2$CH$_2$O—, and —R is H.

7. The compound of claim 2 wherein —X has the structure:

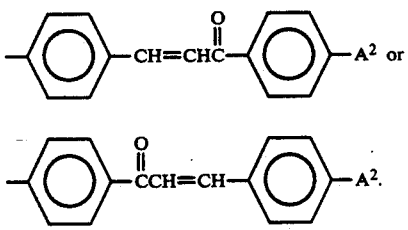

8. The compound of claim 7 wherein —Y— is —OCH$_2$CH$_2$O—, and —R is —H.

9. A sunscreen composition comprising:
   (a) a compound of any one of claims 2, 3, 5 and 7; and
   (b) a cosmetically-acceptable sunscreen carrier.

10. A sunscreen composition comprising:
    (a) from about 1% to about 20% of a compound of any one of claims 2, 3, 5 and 7; and
    (b) a cosmetically-acceptable sunscreen carrier.

11. A method for protecting the skin of humans or lower animals from UVA and UVB wavelength radiation, said method comprising topically applying to the skin of the human or lower animal an effective amount of a sunscreen composition comprising a compound of any one of claims 2, 3, 5 and 7.

* * * * *